United States Patent [19]

Goldman

[11] 4,427,383
[45] Jan. 24, 1984

[54] TOOTH RECONSTRUCTION

[76] Inventor: Melvin Goldman, 34 Brookshire Rd., Worcester, Mass. 01609

[21] Appl. No.: 375,562

[22] Filed: May 6, 1982

[51] Int. Cl.³ ............................................... A61C 5/08
[52] U.S. Cl. ................................................... 433/220
[58] Field of Search ............................... 433/224, 220

[56] References Cited

U.S. PATENT DOCUMENTS

| 400,921 | 4/1889 | Land | 433/225 |
| 1,270,942 | 11/1917 | Grimm | 433/192 |
| 3,732,621 | 3/1971 | Boström | 433/174 |
| 4,084,318 | 4/1974 | McEachern | 433/174 |
| 4,178,686 | 1/1978 | Riess | 433/201 |
| 4,348,183 | 9/1982 | Weissman | 433/174 |

FOREIGN PATENT DOCUMENTS 745543  8/1944  Fed. Rep. of Germany ...... 433/220

Primary Examiner—Robert Peshock
Attorney, Agent, or Firm—Blodgett & Blodgett

[57] ABSTRACT

Apparatus and method for applying a core and crown to a tooth having a cleaned-out root canal, including a threaded post having a nut threaded on and positioned therealong.

2 Claims, 2 Drawing Figures

TOOTH RECONSTRUCTION

BACKGROUND OF THE INVENTION

It is common practice in the reconstruction of a tooth to provide a post that is inserted into the cleaned-out root canal and then building a core of plastic around this post. A crown is formed on the core that fits against what is left of the tooth. In the past, these posts have been formed in various ways. One construction used involves a post which is formed to have a tapered screw, similar to a wood screw, which is rotatably engaged with the root canal; the difficulties is that it is possible to split the tooth when using such a post. In other cases, the post has been serrated and held in place with cement; the difficulty with this method is that it is necessary (in order to lock the upper portion of the reconstruction tooth in place) that there be an enlargement of some kind at the top of the post and the location of this enlargement always presents a problem, since it is not adjustable. These and other difficulties experienced with the prior art devices have been obviated in a novel manner by the present invention.

It is, therefore, an outstanding object of the invention to provide apparatus for restoring a tooth, wherein the post is provided with an adjustable enlargement to lock the core in place.

Another object of this invention is the provision of a post for use in tooth restoration which is capable of engagement in an optimum manner with a cleaned-out root canal.

A further object of the present invention is the provision of a reconstructed tooth involving a cylindrical bore in a root canal and having an undercut counterbore associated with it.

It is another object of the instant invention to provide a tooth restoration post construction which is simple in construction, which is inexpensive to manufacture, and which is capable of a long life of useful service.

It is another object of the instant invention to provide a dental restoration post in which an enlargement on the post is adjustable, so that it can be located at the centroid of the core on which a crown is mounted.

A still further object of the invention is the provision of a tooth reconstruction system in which splitting of the tooth is avoided and in which the core on which the crown is mounted is securely fastened to the remainder of the tooth.

With these and other objects in view, as will be apparent to those skilled in the art, the invention resides in the combination of parts set forth in the specification and covered by the claims appended thereto.

SUMMARY OF THE INVENTION

In general, the present invention involves apparatus for applying a core and crown to a tooth having a cleaned-out root canal, including a threaded post adapted to be cemented in the canal and including a nut threaded onto the post and positioned therealong. The restoration includes the steps of inserting the threaded post in a bore in the root canal and cementing it in place, threading the nut on the post, and forming a plastic core on the post and nut. The nut has been adjusted on the post so that it will be located centrally of the core. An undercut counterbore is formed at the outer end of the bore to lock the core material in place.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
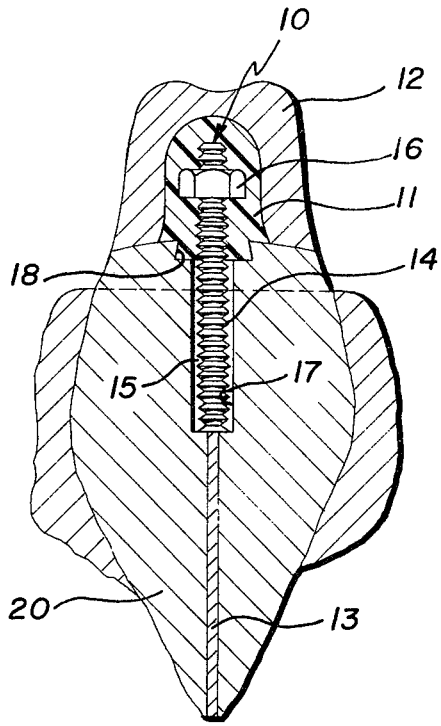
FIG. 1 is a vertical sectional view of a restored tooth incorporating the principles of the present invention.

Referring first to FIG. 1, which best shows the general features of the invention, the apparatus, indicated generally by the reference numeral 10, is used for applying a core 11 and a crown 12 to a tooth 20 having a cleaned-out root canal 13. A threaded post 14 is adapted to be mounted in place in the canal by the use of cement 15. Then, a nut 16 is threaded onto the post and positioned therealong.

More specifically, the root canal 13 is provided with a bore 17 to receive the post 14. A plastic core 11 is built up on the post and nut assembly, while the crown 12 is formed to fit on and be cemented to the core.

The nut 16 is located centrally of the core, both laterally and vertically. Specifically, it should, if possible, be located at the centroid of the solid core shape. The root canal 13 is also provided with a undercut counterbore 18 into which the core material is locked. The undercutting takes the general shape of an internal frusto-conical shape. In the preferred embodiment, the post 14 and the nut 16 are both formed of stainless steel.

Figure 2:
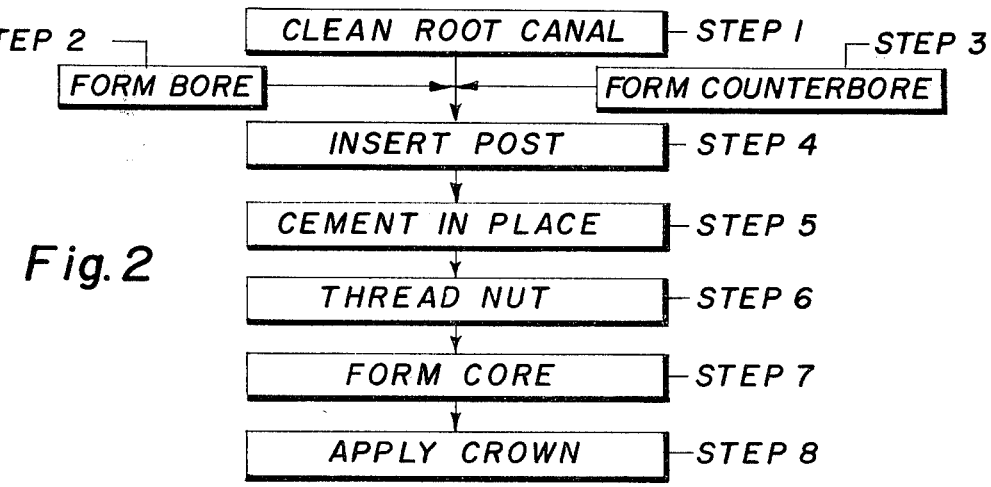
FIG. 2 is a flow chart showing the methods used in the present invention.

FIG. 2 is a flow chart, showing the method of restoring the tooth 20 and is shown as comprising Step 1 which consists of cleaning out the root canal in the general way. The root canal has previously been filled with silver or the like and the cleaning-out process involves the upper part of the root canal. The next step (Step 2) is to form the bore 17, so that its cyla cylindrical bore. In Step 3, the undercut counterbore 18 is formed at the outer end of the bore 17. In Step 4, the post 14 is inserted into the bore 17 and cemented in place. The rotation of the post A while the cement is still soft will force the cement around the inside of the bore 17 and also remove excess cement.

In accordance with Step 5 and Step 6, the nut 16 is threaded in place. It is screwed down to a suitable location, so that it will end up at the center or centroid of the subsequent core 11. An important aspect of the invention is that the nut 16 can be located in the optimum place and this allows the dentist to adjust the height of the core 11. In Step 7, the core 11 is formed and, after the material has hardened, it is possible in Step 8 to apply the crown 12. This is done in the conventional manner by forming a mold in which the crown (which is usually formed of a gold amalgam) is made.

It can be seen, then, that by use of the present apparatus and method, it is possible to obtain a restored tooth in a minimum length of time and with an optimum possibility of the tooth surviving for an extremely long period of time. The danger of splitting the tooth during the separation is minimized, the core is formed in its optimum shape, and is locked in place in the remainder of the tooth. This means that the crown 12, when subsequently applied, is based solidly on the tooth to be restored.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Method of restoring a tooth, comprising the steps of:
   (a) cleaning out a root canal to form a cylindrical bore,
   (b) inserting a threaded post in the bore and cementing it in place,
   (c) threading a nut on the post, the nut being adjusted on the post so as to be located midway between the upper surface of the tooth and the upper end of the post,
   (d) forming a plastic core in a generally smooth configuration on the post and nut,
   (e) making an impression on the said core, and
   (f) applying a crown made from the impression to the core.

2. Method of restoring a tooth as recited in claim 1, wherein an undercut counterbore is formed at the outer end of the bore.

* * * * *